US011617730B2

(12) United States Patent
Goupil

(10) Patent No.: US 11,617,730 B2
(45) Date of Patent: Apr. 4, 2023

(54) PHARMACEUTICAL FORMULATION FOR ADMINISTERING PARACETAMOL BY BUCCAL/GINGIVAL ROUTE

(71) Applicant: Unither Pharmaceuticals, Amiens (FR)

(72) Inventor: Eric Goupil, Paris (FR)

(73) Assignee: Unither Pharmaceuticals

( * ) Notice: Subject to any disclaimer, the term of this patent is extended or adjusted under 35 U.S.C. 154(b) by 85 days.

(21) Appl. No.: 16/489,378

(22) PCT Filed: Feb. 28, 2018

(86) PCT No.: PCT/EP2018/054949
§ 371 (c)(1),
(2) Date: Aug. 28, 2019

(87) PCT Pub. No.: WO2018/158324
PCT Pub. Date: Sep. 7, 2018

(65) Prior Publication Data
US 2019/0374488 A1 Dec. 12, 2019

(30) Foreign Application Priority Data
Feb. 28, 2017 (FR) ....................................... 1751652

(51) Int. Cl.
| A61K 9/00 | (2006.01) |
| A61K 31/167 | (2006.01) |
| A61K 47/02 | (2006.01) |
| A61K 47/10 | (2017.01) |

(52) U.S. Cl.
CPC ............ *A61K 31/167* (2013.01); *A61K 9/006* (2013.01); *A61K 47/02* (2013.01); *A61K 47/10* (2013.01)

(58) Field of Classification Search
CPC .... A61K 9/0053; A61K 9/0056; A61K 9/006; A61K 9/0063; A61K 9/0012
See application file for complete search history.

(56) References Cited

U.S. PATENT DOCUMENTS

| 2002/0168334 A1* | 11/2002 | Jacob | ..................... | A61K 47/36 424/78.31 |
| 2010/0093710 A1* | 4/2010 | Perovitch | ................ | A61P 25/00 514/226.2 |
| 2011/0275626 A1 | 11/2011 | Perovitch et al. | | |

FOREIGN PATENT DOCUMENTS

| EP | 2101730 A2 | 9/2009 |
| EP | 2387389 A1 | 11/2011 |
| WO | 2008087323 A2 | 7/2008 |
| WO | 2010081984 A1 | 7/2010 |

OTHER PUBLICATIONS

EDinformatics: Solutions, Suspensions and Colloids—Summary Tables (Year: 1999).*
Codling, et al., Diffusion Studies of Dihydroxybenzene Isomers in Water?Alcohol Systems, The Journal of Physical Chemistry B, Feb. 2013, pp. 2734-2741, vol. 117, American Cheminacl Society.
Edward, Molecular Volumes and the Stokes-Einstein Equation, Journal of Chemical Education, Apr. 1970, pp. 261-270, vol. 47, No. 4.
Einstein, On The Movement of Small Particles Suspended in Stationary Liquids Required by the Molecular-Kinetic Theory of Heat, Annalen Der Physik 17, May 1905, pp. 549-560.
Einstein, On the Theory of Brownian Motion, Annalen Der Physik 19, Jan. 1906, pp. 371-381.
International Search Report for Application No. PCT/EP2018,054949, dated May 18, 2018, pp. 1-3.
Khattab, et al., Density, viscosity, and surface tension of water+ ethanol mixtures from 293 to 323K, Korean J. Chem. Eng., Jun. 2012, pp. 812-817, vol. 29, No. 6.
Morris, et al., Resolution of Discrete and Continuous Molecular Size Distributions by Means of Diffusion-Ordered 2D NMR Spectroscopy, J. Am. Chem. Soc., May 1993, pp. 4291-4299, vol. 115.
Pickering, et al., A New Transmucous-Buccal Formulation of Acetaminophen for Acute Traumatic Pain: A Non-inferiority, Randomized, Double-Blind, Clinical Trial, Pain Physician Journal, May/Jun. 2015, pp. 249-257, vol. 18.
Price, et al., Solution Dynamics in Aqueous Monohydric Alcohol Systems, J. Phys. Chem. A, Published on web May 2003, pp. 4784-4789, vol. 107.
Weksler, et al., Blood-brain barrier-specific properties of a human adult brain endothelial cell line, The FASEB Journal, Nov. 2005, pp. 1872-1874, vol. 19.
Weksler, et al., The hCMEC/D3 cell line as a model of the human blood brain barrier, Fluids and Barriers of the CNS, Mar. 2013, pp. 1-10, vol. 10, No. 16.

* cited by examiner

*Primary Examiner* — Micah Paul Young
(74) *Attorney, Agent, or Firm* — Lerner, David, Littenberg, Krumholz & Mentlik, LLP

(57) ABSTRACT

The present invention concerns a pharmaceutical formulation for administering paracetamol by buccal/gingival route consisting of a hydroalcoholic solution comprising dissolved paracetamol, characterised in that: #the mass of paracetamol is between 95 mg and 190 mg, #the volume of said hydroalcoholic solution is between 1.0 ml and 2.0 ml, #the degree of alcohol of said hydroalcoholic solution is between 48.5° and 52.5°, and #the concentration of paracetamol in said hydroalcoholic solution is between 85 mg/ml and 110 mg/ml. The present invention also concerns said pharmaceutical formulation for the use of same for accelerating the speed at which paracetamol passes through the blood-brain barrier, and the use thereof as a drug, in particular for the symptomatic treatment of pain or fever.

6 Claims, 7 Drawing Sheets

PHARMACEUTICAL FORMULATION FOR ADMINISTERING PARACETAMOL BY BUCCAL/GINGIVAL ROUTE

CROSS-REFERENCE TO RELATED APPLICATIONS

The present application is a national phase entry under 35 U.S.C. § 371 of International Application No. PCT/EP2018/054949 filed Feb. 28, 2018, which claims priority from French Application No. 1751652 filed Feb. 28, 2017, all of which are hereby incorporated herein by reference.

FIELD OF THE INVENTION

The present invention concerns a pharmaceutical formulation for the buccal/gingival administration of paracetamol, as well as its use to accelerate the crossing of the blood-brain barrier by paracetamol, and its use as a drug, in particular for the treatment of pain and/or fever.

STATE OF THE ART

Paracetamol is an active ingredient that has been used for many years to relieve mild to moderate pain and/or fever.

Although its mechanism of action is still not known in detail, this product is one of the most widely used medicinal products in the world due to its very favorable risk-benefit ratio.

However, its favorable risk-benefit ratio has made its use too common, leading to many accidental overdoses, particularly in the USA, where this compound is systematically added to consumer drug formulations. Consumers taking several medicinal products can eventually induce overdoses and fatal poisonings.

The United States Food and Drug Administration (FDA) has in fact alerted pharmaceutical companies to reduce doses of paracetamol in combination products.

In 2014, the FDA banned the marketing of all products combined with other active ingredients containing more than 325 mg of paracetamol, in order to limit the risk of poisoning and fatal accidents.

It is therefore necessary to develop medicinal products whose optimized formulation improves the efficacy of paracetamol in order to reduce the doses necessary to obtain an effective analgesic effect.

In patent application WO2008/087323 very specific formulations of paracetamol have been disclosed, which aim to allow a reduction in the dose of paracetamol while maintaining the efficacy of the product.

This patent application describes a dosage form for transmucosal administration of paracetamol, which comprises between 25 mg and 250 mg of paracetamol in a hydroalcoholic solution having a volume between 0.5 mL and 2.5 mL.

Thus, the concentration of paracetamol in said dosage form varies between 10 mg/mL and 500 mg/mL.

However, the Applicant has discovered, on the one hand, that a concentration of paracetamol lower than 85 mg/mL required the administration of an excessive volume of solution, incompatible with buccal/gingival administration in that it triggered a swallowing reflex. This amounts to administering the active ingredient orally, whereby the active ingredient must pass through the digestive system and the liver to reach the bloodstream and undergoes a metabolism (chemical or biological) known as hepatic first-pass metabolism.

On the other hand, the Applicant has found in stability studies that paracetamol recrystallizes over time if its concentration is too high, typically above 125 mg/mL. In addition, pre-stability studies for 6 months at 40° C. have shown the appearance of pink coloration if the concentration is greater than 115 mg/mL, which is related to polymerization of paracetamol in the hydroalcoholic solution by electro-oxidation.

In addition, in the dosage form of the prior art, the alcohol content of the hydroalcoholic solution can vary between 10° and 70°.

However, the Applicant has discovered that a hydroalcoholic solution in which the volume of ethanol represents 60% or more of the total volume of said solution is likely to cause problems of physiological intolerance of the mucous membranes. Moreover, if, on the other hand, the percentage by volume of ethanol in relation to the total volume of the water/ethanol mixture is too low, typically less than 45%, the dissolution of paracetamol is compromised, insofar as paracetamol dissolves more easily in ethanol than in water.

Consequently, the Applicant has developed a novel pharmaceutical formulation for the buccal/gingival administration of paracetamol, which avoids the various pitfalls previously listed.

Surprisingly, the pharmaceutical formulation optimized by the Applicant has very specific physicochemical characteristics, which translate into high therapeutic efficacy. Indeed, a contraction of the paracetamol molecule in the formulation according to the invention has been demonstrated, which helps its passage through the buccal mucous membranes. In addition, the formulation developed by the Applicant makes it possible to actively transport paracetamol molecules across the blood-brain barrier with a very high crossing capacity compared with conventional formulations, in particular existing aqueous injectable solutions, such as Perfalgan. This helps improve the therapeutic efficacy of paracetamol by targeting its delivery to the central nervous system.

SUMMARY OF THE INVENTION

A first subject-matter of the present invention therefore relates to a pharmaceutical formulation for the buccal/gingival administration of paracetamol consisting of a hydroalcoholic solution comprising dissolved paracetamol, wherein:
  the mass of paracetamol is between 95 mg and 190 mg,
  the volume of said hydroalcoholic solution is between 1.0 mL and 2.0 mL
  the alcohol content of said hydroalcoholic solution is between 48.5° and 52.5°, and
  the concentration of paracetamol in said hydroalcoholic solution is between 85 mg/mL and 110 mg/mL.

A second subject-matter of the present invention relates to said pharmaceutical formulation for use to accelerate the crossing of the blood-brain barrier by paracetamol.

A third subject-matter of the present invention relates to said pharmaceutical formulation for use as a drug, in particular for the symptomatic treatment of pain or fever.

Definitions

For the purposes of the present invention, "buccal/gingival" means a route of drug administration by which the active ingredient is administered in the mouth. It diffuses through the buccal mucosa and enters directly into the bloodstream. Depending on the type of absorption, the sublingual or perlingual route can be distinguished.

For the purposes of the present invention, "dissolved paracetamol" means paracetamol in its molecular state and weakly ionized in its solvent, in a state of complete and stable dissolution over time.

For the purposes of the present invention, the "blood-brain barrier" refers to the physiological barrier present in the brain in all terrestrial vertebrates between the circulating blood and the central nervous system (CNS), which allows homeostasis to be maintained in the brain by separating it from the blood. It is also called It is also called the hemoencephalic or hemato-meningeal barrier. The essential components of this barrier are the endothelial cells that line the capillaries on the blood flow side and are connected to each other by tight junctions.

PRESENTATION OF THE FIGURES

FIGS. 1A and 1B reproduce the results of a DOSY experiment performed on sample EU-95.

FIG. 1A shows more precisely the plot of signal strength ($CH_3$ of paracetamol) as a function of magnetic field gradient strength.

FIG. 1B corresponds to the DOSY $^1$H-NMR spectrum recorded at 400 MHz, at 25° C., 8 scans for 16 gradient increments, dl=2 s, LB=5 Hz. The horizontal dimension represents the chemical shifts of the protons of the compounds in the mixture, the vertical dimension the diffusion coefficients, after Laplace transformation.

FIGS. 2A and 2B represent the hydrodynamic radius of water, of ethanol and viscosity during ethanol-in-water dilution experiments, at 25° C. and 40° C. respectively. $R_H$ (±0.1 Å) is calculated from the DOSY $^1$H-NMR diffusion coefficient measurements. Viscosity values are taken from the literature [Khattab et al. (2012) *Korean J. Chem. Eng.* 29, 812-817]. The shaded area corresponds to the mole fractions studied in the presence of paracetamol.

FIGS. 3A and 3B represent the hydrodynamic radius of water, of ethanol, of paracetamol and viscosity for samples EU-95, EU-95-30, EU-95-50 and EU-95-80, at 25° C. and 40° C. respectively. $R_H$ (±0.1 Å) is calculated from the DOSY $^1$H-NMR diffusion coefficient measurements. Viscosity values are taken from the literature [Khattab et al. (2012) *Korean J. Chem. Eng.* 29, 812-817].

FIG. 4 is a schematic representation of the device used for the cellular model mimicking the blood-brain barrier. It is a transwell system.

FIG. 5 shows the flow of paracetamol across the in vitro blood-brain barrier model as a function of time in the following four situations:
US: paracetamol comes from solution U 95, the culture medium contains 5% saline;
U: paracetamol comes from solution U 95, the culture medium does not contain saline;
PS: paracetamol comes from Perfalgan, the culture medium contains 5% saline; and
P: paracetamol comes from Perfalgan, the culture medium does not contain saline.

DETAILED DESCRIPTION OF THE INVENTION

Figure 1A:
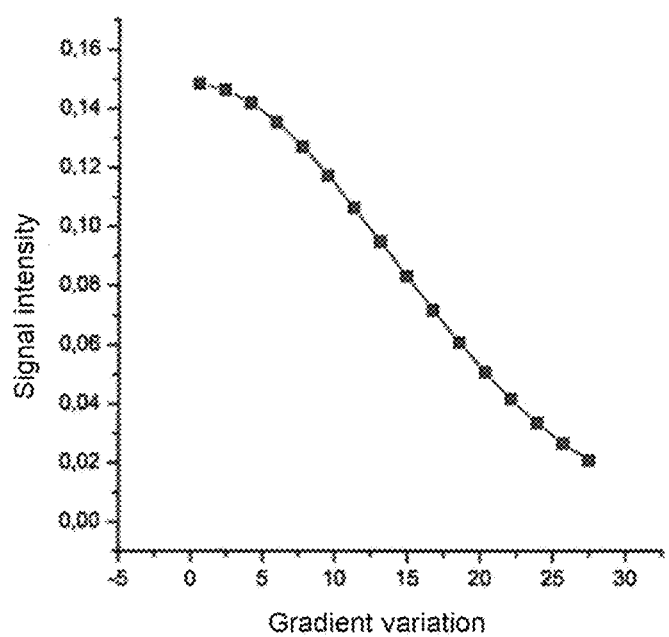

The present invention first relates to a pharmaceutical formulation for the buccal/gingival administration of paracetamol consisting of a hydroalcoholic solution comprising dissolved paracetamol, wherein:
the mass of paracetamol is between 95 mg and 190 mg,
the volume of said hydroalcoholic solution is between 1.0 mL and 2.0 mL,
the alcohol content of said hydroalcoholic solution is between 48.5° and 52.5°, and
the concentration of paracetamol in said hydroalcoholic solution is between 85 mg/mL and 110 mg/mL.

Advantageously, the mass of paracetamol is between 120 mg and 170 mg, typically between 125 mg and 165 mg, and is in particular equal to 125 mg or 165 mg.

Preferably, the volume of the hydroalcoholic solution is between 1.2 mL and 1.7 mL, typically between 1.25 mL and 1.65 mL, and is in particular equal to 1.25 mL or 1.65 m L.

Advantageously, the concentration of paracetamol in said hydroalcoholic solution is between 90 mg/mL and 105 mg/mL, preferably between 95 mg/mL and 105 mg/mL, and is in particular equal to 100 mg/mL.

Preferably, the hydroalcoholic solution consists of a water/ethanol mixture, in which the volume of ethanol represents between 45% and 60% of the total volume of said hydroalcoholic solution, advantageously between 48.5% and 52.5%, typically 50%.

In the context of the present invention, "ethanol" refers to a commercial binary solution consisting of water and ethanol, and containing 96% to 99.8% (by volume) ethanol, advantageously 96% (by volume) ethanol.

Advantageously:
the mass of paracetamol is between 120 mg and 170 mg, typically between 125 mg and 165 mg,
the volume of the hydroalcoholic solution is between 1.2 mL and 1.7 mL, typically between 1.25 mL and 1.65 mL, and
the hydroalcoholic solution consists of a water/ethanol mixture, wherein the volume of ethanol represents between 50% of the total volume of said hydroalcoholic solution.

In a first particular embodiment:
the mass of paracetamol is equal to 125 mg,
the volume of the hydroalcoholic solution is equal to 1.25 mL, and
the hydroalcoholic solution consists of a water/ethanol mixture, wherein the volume of ethanol represents 50% of the total volume of said hydroalcoholic solution.

In a second particular embodiment:
the mass of paracetamol is 165 mg,
the volume of the hydroalcoholic solution is 1.65 mL, and
the hydroalcoholic solution consists of a water/ethanol mixture, wherein the volume of ethanol represents 50% of the total volume of said hydroalcoholic solution.

Preferably, the viscosity of the hydroalcoholic solution is greater than $1.5 \cdot 10^{-3}$ Pa·s.

Advantageously, the hydrodynamic radius at 40° C. of the paracetamol dissolved in the hydroalcoholic solution as defined above is less than 2.1 Å.

For the purposes of the present invention, "hydrodynamic radius", or $R_H$, means the radius of a solute in solution, said solute being assumed to be spherical, as defined by the following Stokes-Einstein relation [Edward, J. T. (1970) *J. Chem. Educ.* 47, 261; Einstein, A. (1905) *Annalen Der Physik* 17, 549-560; Einstein, A. (1906) *Annalen Der Physik* 19, 371-381]:

$$D = \frac{k_B T}{6\pi \rho R_H} \text{ where:}$$

D is the diffusion coefficient of the solute in the solvent (expressed in $m^2 \cdot s^{-1}$), $k_B$ is the Boltzmann constant, and is $k_B = 1.3806 \cdot 10^{-23}$ $J \cdot K^{-1}$, T is the temperature of the medium (expressed in K), ρ is the viscosity of the medium (expressed in Pa·s, or equivalent in $kg \cdot s^{-1} \cdot m^{-1}$), and $R_H$ is expressed in m.

The measurement of the diffusion coefficient in solution of a molecule considered spherical thus makes it possible to determine the size of the molecule, more precisely its hydrodynamic radius.

In a particular embodiment, the hydroalcoholic solution includes a flavoring and/or a sweetener.

For the purposes of the present invention, a "flavoring and/or a sweetener" is defined as any pharmaceutically acceptable substance that makes more pleasant the taste perceived by the patient to whom the pharmaceutical formulation is administered. "Pharmaceutically acceptable" means what is generally safe, non-toxic and neither biologically nor otherwise undesirable, and which is acceptable for both veterinary and human pharmaceutical use.

In a particular embodiment, the hydroalcoholic solution contains at least one active ingredient other than paracetamol.

In particular, any lipophilic substance capable of providing an adjuvant that is analgesic, decongestant, sedative for the airways, sinuses, rhino and oropharyngeal pathways, which is compatible with dissolution in a hydroalcoholic solution, may be combined with paracetamol. In particular, paracetamol may be combined with pseudoephedrine, triprolidine, promethazine, pheniramine, meclizine, diphenhydramine, dimenhydrinate, cyproheptadine, dextropropoxyphene, and/or codeine.

In addition, the present invention also relates to a pharmaceutical formulation as defined above for use to accelerate the crossing of the blood-brain barrier by paracetamol.

Finally, the present invention also relates to a pharmaceutical formulation as defined above, for use as a drug, in particular for the treatment of pain, typically mild to moderate, and/or fever.

The pharmaceutical formulation according to the invention may be packaged in a single-dose package of 0.5 to 3 mL, which package must limit the adsorption of paracetamol on its surface, be impermeable to the hydroalcoholic solution, and guarantee the stability of the solution, while allowing the complete delivery of the pharmaceutical formulation to the mandibular vestibule.

Examples

The following abbreviations have been used:
C: concentration
EBM2: Endothelial Basal Medium 2
HEPES: 4-(2-hydroxyethyl)-1-piperazine ethane sulfonic acid
HPLC: High-performance liquid chromatography
PTFE: Polytetrafluoroethene
QS: As much as suffices
NMR: Nuclear Magnetic Resonance
2D $^1$H-NMR: Two-dimensional proton NMR
v/v: volume ratio
$x_E$: mole fraction of ethanol in water 1. Effect of Dilution of the Hydroalcoholic Solution on the Hydrodynamic Radius of Paracetamol Materials and Methods Materials A. Paracetamol Solutions U 95: 95 mg/ml paracetamol solution in a water/ethanol mixture (50/50 v/v) (C=628 mM), and PERFALGAN: 10 mg/mL commercial paracetamol solution for infants and children+excipients (C=66 mM).

B. References

Ethanol (lot MPA1003583): 10 mL vial,

Paracetamol powder (lot MPA10031465): 1 g (M=151.16 g/mol),

Heavy water ($D_2O$): purchased from Eurisotop (Groupe CEA, Saclay),

Saline (Gilbert Laboratoires): aqueous solution containing 0.9 g/100 mL (C=154 mM) sodium chloride in 5 mL dose units, and Milli-Q water, produced with a filtration and reverse osmosis system from Millipore (Molsheim, France).

Preparation of Samples

For NMR analyses of the liquid, the following samples were prepared and placed in 5 mm diameter glass NMR tubes or 4 mm diameter zirconia rotors (Cortecnet, France). A small amount of heavy water ($D_2O$) is added to ensure spatial and temporal homogeneity during acquisitions.

EU-95: 450 μL U 95+50 μL $D_2O$ (C=565 mM, $x_E$=0.236),

EU-95-30: 500 μL U 95+215 μL saline+70 μL $D_2O$ (C=400 mM, $x_E$=0.141),

EU-95-50: 250 μL U 95+250 μL saline+50 μL $D_2O$ (C=285 mM, $x_E$=0.092),

EU-95-80: 250 μL U 95+1250 μL saline+150 μL $D_2O$ (C=95 mM, $x_E$=0.033),

REF-Saline: 450 μL saline+50 μL $D_2O$ ($C_{NaCl}$=138 mM, $x_E$=0.0),

REF: 250 μL EtOH+250 μL Milli-Q water+50 μL $D_2O$ (C=6.9 M, $x_E$=0.236),

REF-30: 250 μL EtOH+250 μL Milli-Q water+215 μL saline+70 μL $D_2O$ (C=4.8 M, $x_E$=0.141), REF-50: 125 μL EtOH+125 μL Milli-Q water+215 μL saline+50 μL $D_2O$ (C=3.7 M, $x_E$=0.092), REF-80: 125 μl EtOH+125 μL Milli-Q water+1250 μL saline+150 μL $D_2O$ (C=1.14 M, $x_E$=0.033), REF-EtOH: 450 μL EtOH (C=13.6 M, $x_E$=0.999), PERF: 450 μL Perfalgan+50 μL $D_2O$ (C=59 mM, $x_E$=0.0), and PARA-125: 56 mg paracetamol powder+500 μL EtOH+50 μL $D_2O$ (C=673 mM, $x_E$=0.735).

Methods

The Bruker SB 400 MHz NMR spectrometer (Wissembourg, France) equipped with a QNP SB $^1$H/$^{19}$F—$^{13}$C—$^{31}$P probe operating in static mode was used to perform liquid proton NMR analyses.

In 2D $^1$H-NMR, the sequence used is a DOSY pulse sequence [Morris, K. F., and Johnson, C. S. (1993) *J. Am. Chem. Soc.* 115, 4291-4299] (spin-echo sequence with Z gradient), with regulation of the temperature at +0.5° C. The 90° pulse is 15 μs, the recycling time is 5 s, the number of acquisitions is 48 with 16 increments for the gradient, for a total acquisition time of 1 hour. The signals are filtered with a decreasing exponential function of constant 2 Hz, before Fourrier transformation in the F2 dimension ($^1$H chemical shift). An inverse Laplace transform is performed in the F1 dimension and gives the diffusion coefficients directly.

The software used for NMR spectrum processing is Topspin 2.0 developed by Bruker.

Results

Introductory Remark

The sizes of molecules in solution can be estimated by liquid NMR using so-called diffusion experiments to measure the diffusion coefficients of species in solution. The experiment is performed by applying a magnetic field gradient in a given direction, the direction in which the diffusion of particles is measured.

Figure 1B:
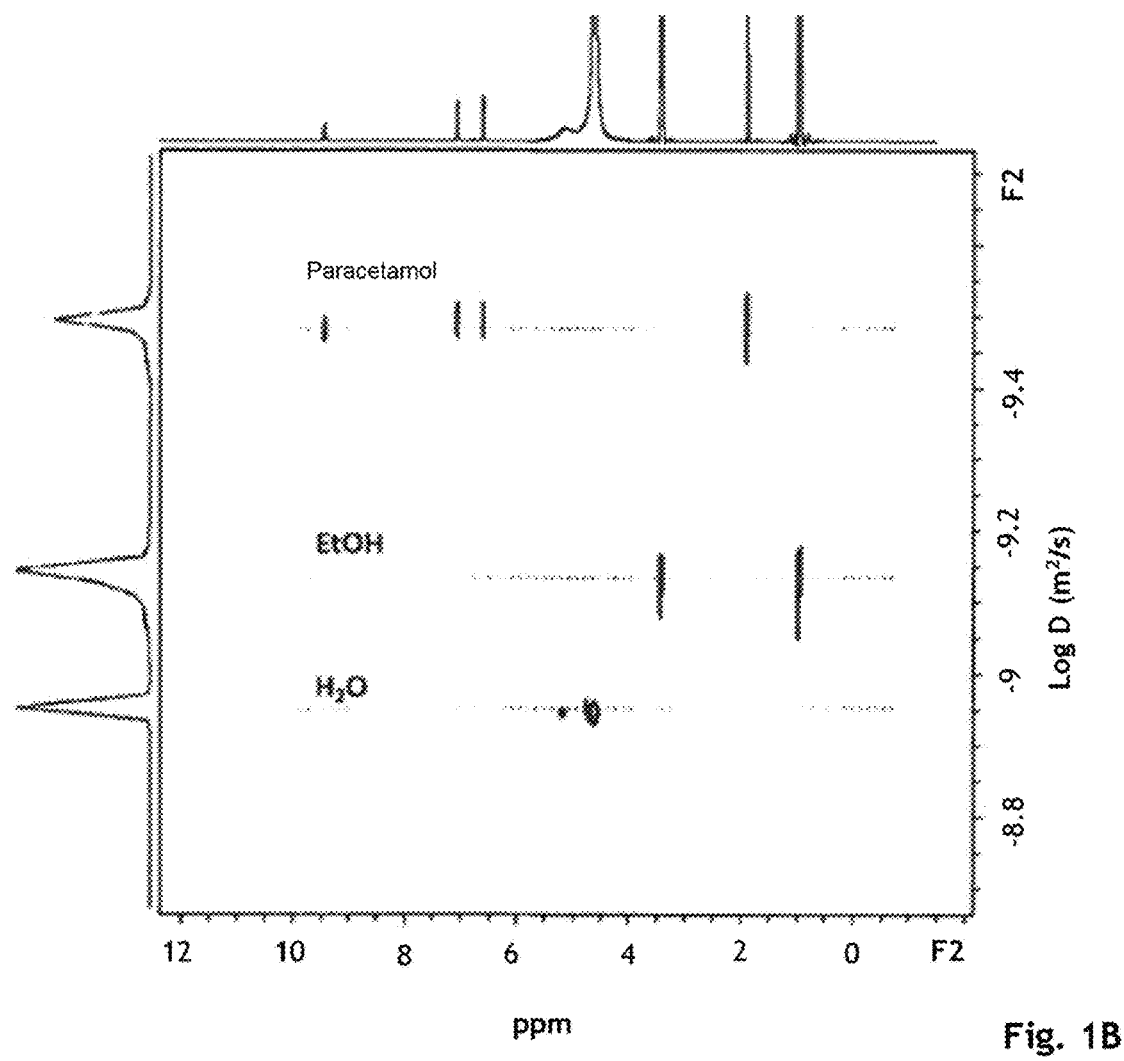

Two treatments are possible following this type of experiment. Peak by peak analysis can be performed by very precisely setting the variation in intensity of NMR peaks as a function of the field gradient (FIG. 1A). The only adjustment variable being the diffusion coefficient, it is then easy to obtain the size of the species in solution using the Stokes-Einstein equation already described. A Laplace transform can also be applied to obtain on a two-dimensional map (2D-NMR), chemical diffusion/shift, the diffusion coefficient being directly measurable along the y axis (FIG. 1B).

Measurement of Diffusion Coefficients of Reference Samples

The DOSY experiments were conducted on water, ethanol, Perfalgan and paracetamol solubilized in ethanol.

For the measurement of diffusion coefficients, an NMR resonance is chosen, usually $CH_3$ which is isolated, because it provides more accuracy. In this case the accuracy is estimated at $\pm 0.1 \cdot 10^{-9}$ m$^2$·s$^{-1}$.

The values of the diffusion coefficients of the different compounds that have been determined are shown in Table 1 below. This table also includes viscosity values obtained from the literature [Khattab, I. S., Bandarkar, F., Fakhree, M. A. A., and Jouyban, A. (2012) Korean J. Chem. Eng. 29, 812-817], the mole fraction of ethanol and the hydrodynamic radius calculated from the Stokes-Einstein equation. The accuracy of the value thus calculated is estimated at $\pm 0.1$ Å.

TABLE 1

Measurement of diffusion coefficients by DOSY $^1$H-NMR, at 25° C., on reference samples.

| SAMPLE | Mole fraction Ethanol, $x_E$ | Viscosity 25° C. ($10^{-3}$ Pa · s) | Observed NMR resonance | D 25° C. ($10^{-9}$ m$^2$ · s$^{-1}$) | $R_H$ 25° C. (Å) |
|---|---|---|---|---|---|
| REF-Saline | 0 | 0.8914 | H$_2$O | 2.4 | 1.0 |
| PERF | 0 | 0.8914 | CH$_3$ Paracetamol | 0.9 | 2.8 |
|  |  |  | H$_2$O | 2.6 | 0.9 |
|  |  |  | Mannitol | 0.8 | 3.2 |
| REF-EtOH | 0.999 | 1.0995 | CH$_3$ Ethanol | 1.2 | 1.7 |
|  |  |  | H$_2$O (traces) | 1.3 | 1.5 |
| PARA-125 | 0.735 | 1.6594 | CH$_3$ Ethanol | 0.7 | 1.8 |
|  |  |  | CH$_3$ Paracetamol | 0.3 | 4.2 |
|  |  |  | H$_2$O | 0.8 | 1.5 |

Measurement of the Diffusion Coefficients of Water-EtOH Solutions During Dilution with Water (Saline Solution)

From the experiments on the reference samples, it appears that the size of the molecules varies from one sample to another, depending very strongly on the solvent: for example, paracetamol has an $R_H$ of 2.8 Å in the Perfalgan sample, and an $R_H$ of 4.2 Å in ethanol.

The viscosity of the sample and complex hydration phenomena are involved here. It is important to monitor the molecule sizes in the different solvents in the study and in particular during dilution studies.

The reference solutions (REF-Saline, REF, REF-30, REF-50, REF-80 and REF-EtOH) were therefore subjected to DOSY experiments to evaluate the effect of dilution with water.

Figure 2A:
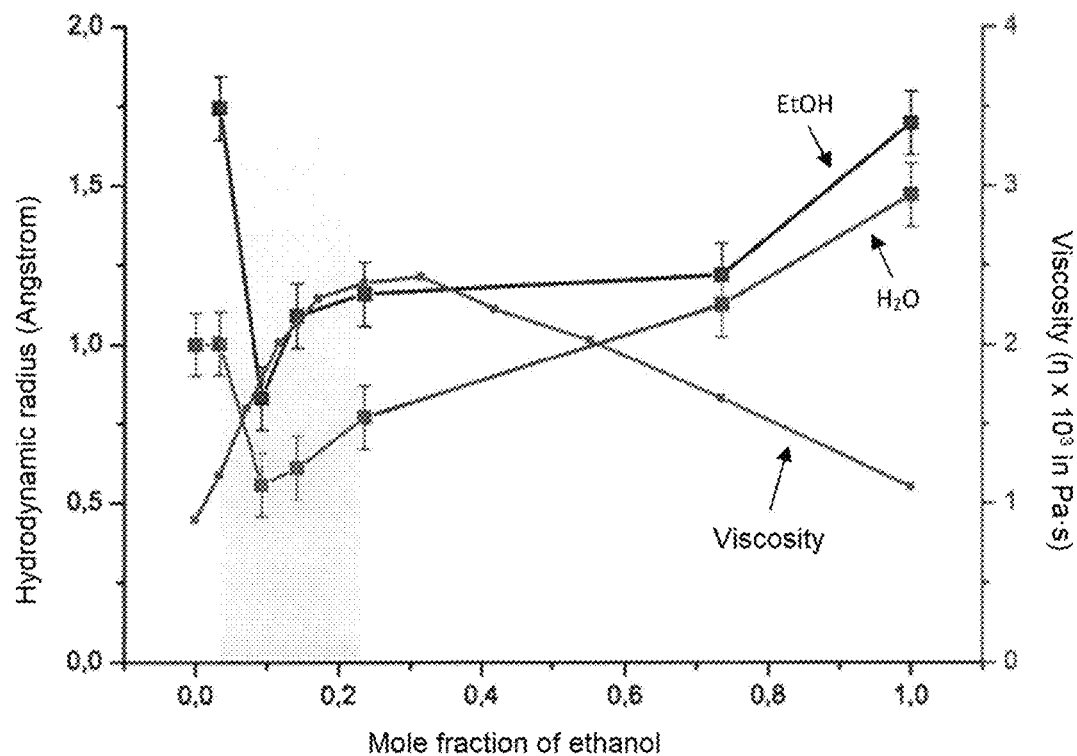
Figure 2B:
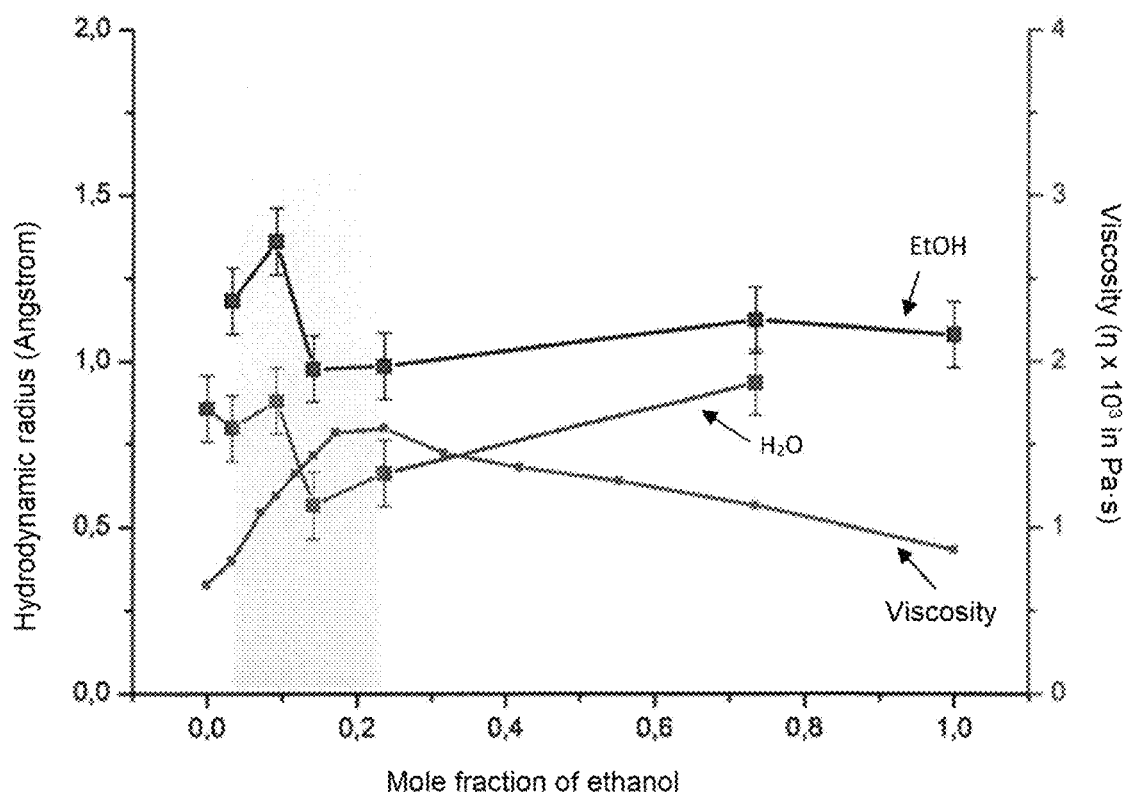

The results obtained at 25° C. and 40° C. are shown in FIGS. 2A and 2B, respectively.

Several conclusions can be drawn from such results.

The viscosity has a maximum for an EtOH/Water mole fraction close to 0.3 (60/40 v/v) at 25° C. and close to 0.2 (50/50 v/v) at 40° C. This is remarkable and indicates that the maximum viscosity is 2 to 3 times higher than that of pure water or of pure ethanol.

The hydrodynamic radii calculated for water and ethanol also have a particular behavior. While ethanol has a radius of 1.5 Å at 25° C., in both pure and highly diluted form, it has a minimum (0.8 Å) to $x_E$ of between 0.05 and 0.1. Water behaves in the same way. This phenomenon has already been encountered in the literature [Price, W. S., Ide, H., and Arata, Y. (2003) The Journal of Physical Chemistry A 107, 4784-4789; Codling, D. J., Zheng, G., Stait-Gardner, T., Yang, S., Nilsson, M., and Price, W. S. (2013) The Journal of Physical Chemistry B 117, 2734-2741] and is explained by the breaking, in the mixture, of water-water or ethanol-ethanol associations found for pure solutions of water or ethanol.

At 40° C., viscosity and $R_H$ are lower than at 25° C., which reflects the effect of temperature: Brownian motion tends to break hydrogen bonds, which has the effect of destroying all the dipole-dipole associations that water and ethanol can form together.

Interestingly, sample EU-95 has a mole fraction of ethanol of 0.236, i.e. in the area where the viscosity has a maximum.

Figure 3A:
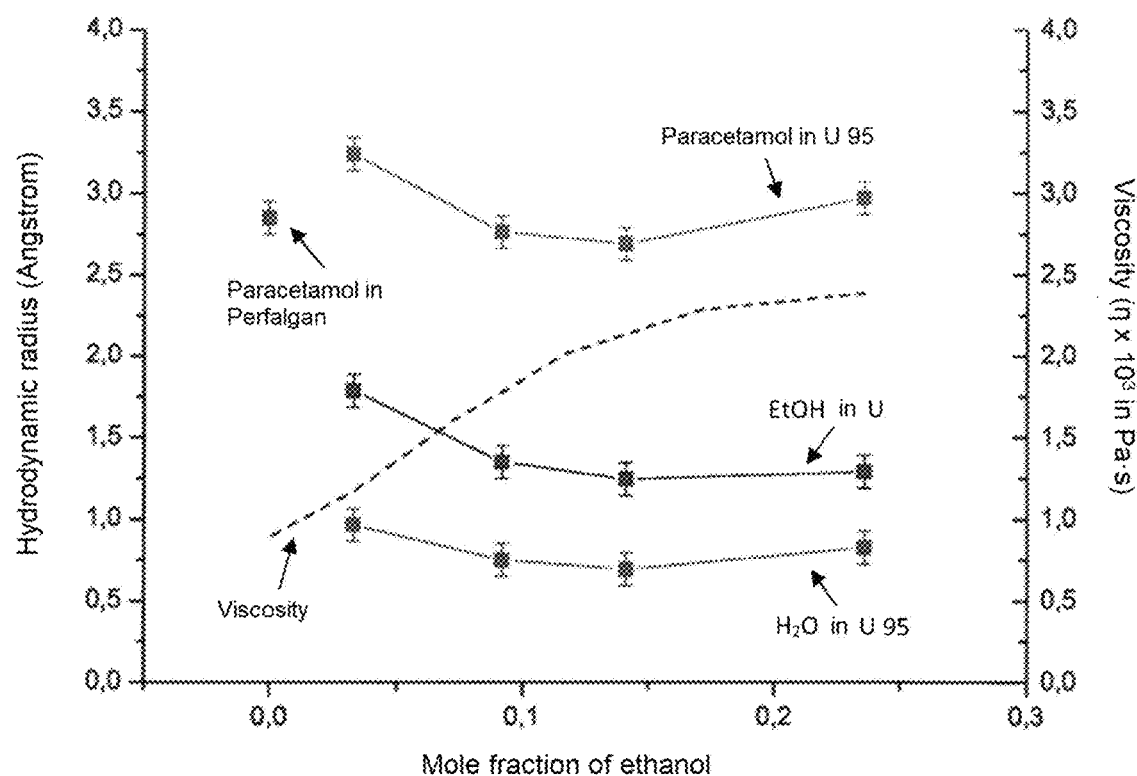
Figure 3B:
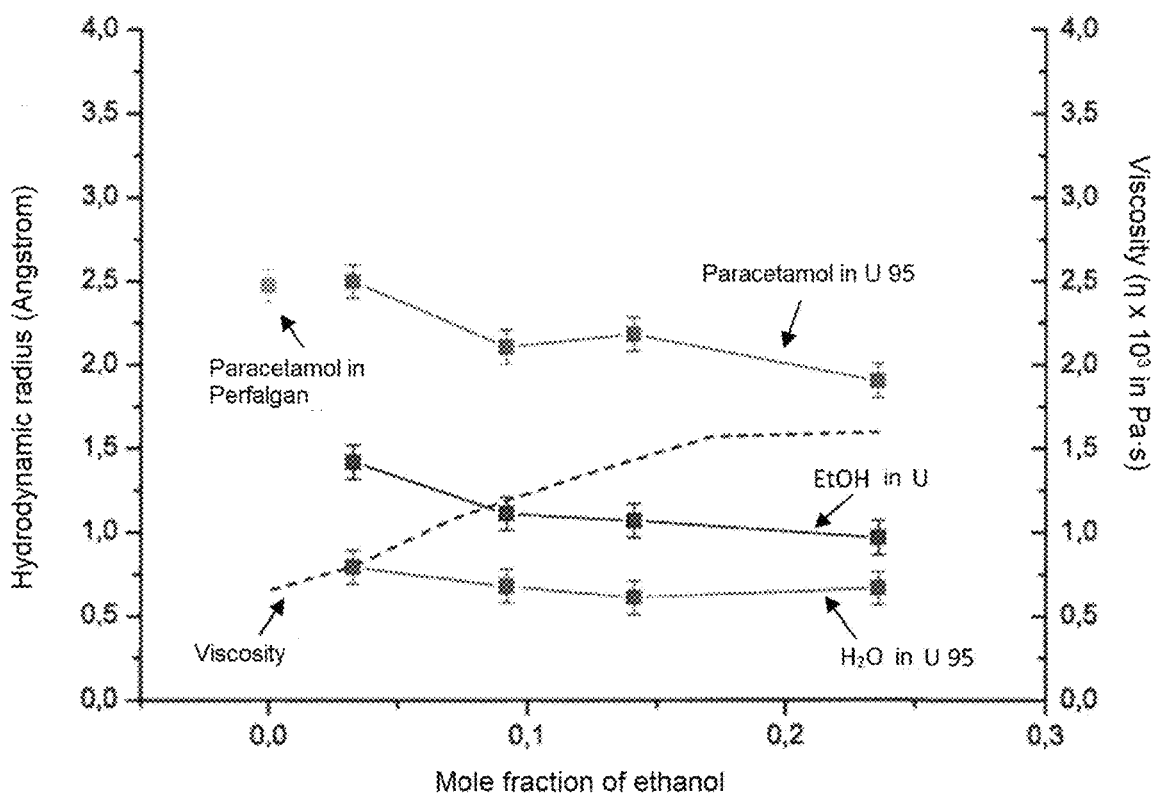

Measurement of the Diffusion Coefficients of Water-ETOH-Paracetamol Solutions when Diluted with Water (Saline Solution) or when the Concentration of Paracetamol in the Same Hydroalcoholic Medium Decreases Solutions containing paracetamol under different dilution conditions (EU-95, EU-95-30, EU-95-50 and EU-95-80) were also subjected to DOSY experiments. These solutions correspond to $x_E$ values of 0.236, 0.141, 0.092 and 0.033, respectively, which define the shaded area in FIGS. 2A and 2B. The results obtained at 25° C. and 40° C. are compiled in Table 2 below and reported in FIGS. 3A and 3B, respectively.

At 40° C., the temperature closest to that of the human body, the lowest hydrodynamic radius of paracetamol (1.9 Å) is obtained for the undiluted sample of U 95 (EU-95). It differs from the value of paracetamol in Perfalgan (2.5 Å) which is little affected by temperature rise.

TABLE 2

Measurement of diffusion coefficients by DOSY $^1$H-NMR, at 25° C. and 40° C., on Perfalgan and U-95 (95 mg/mL) samples during dilutions.

| SAMPLE | Mole fraction Ethanol, $x_E$ | Viscosity ($10^{-3}$ Pa·s) 25° C. 40° C. | Observed NMR resonance | D ($10^{-9}$ m$^2$·s$^{-1}$) 25° C. 40° C. | $R_H$ (Å) 25° C. 40° C. |
|---|---|---|---|---|---|
| PERF | 0 | 0.8914 0.8914 | CH$_3$ Paracetamol H$_2$O | 0.9 1.4 2.6 4.4 | 2.8 2.5 1.0 0.8 |
| EU-95 | 0.236 | 2.3869 1.5924 | CH$_3$ Ethanol CH$_3$ Paracetamol H$_2$O | 0.7 1.5 0.3 0.8 1.1 2.2 | 1.3 1.0 3.0 1.9 0.8 0.7 |
| EU-95-30 | 0.141 | 2.1337 1.4299 | CH$_3$ Ethanol CH$_3$ Paracetamol H$_2$O | 0.8 1.5 0.4 0.7 1.5 2.6 | 1.2 1.1 2.7 2.2 0.7 0.6 |
| EU-95-50 | 0.092 | 1.7759 1.1862 | CH$_3$ Ethanol CH$_3$ Paracetamol H$_2$O | 0.9 1.7 0.4 0.9 1.6 2.8 | 1.4 1.1 2.8 2.1 0.8 0.7 |
| EU-95-80 | 0.033 | 0.9855 1.7975 | CH$_3$ Ethanol CH$_3$ Paracetamol H$_2$O | 1.2 0.2 0.7 1.1 2.3 3.6 | 1.8 1.4 3.2 2.5 1.0 0.8 |

Conclusion

Hydroalcoholic solutions are distinguished by particular macroscopic and molecular aspects, and the paracetamol molecules dissolved in such solutions have remarkable properties.

Water forms a network of pure hydrogen bonds and ethanol forms pure alcohol-alcohol associations. Very low alcohol contents in water lead to water/ethanol associations. For higher ethanol contents, there is a break in the associations and the molecules behave individually, isolated from each other in the mixture.

At the same time, the viscosity of the solution increases, to reach a maximum for an EtOH/Water mole fraction close to 0.3 (60/40 v/v) at 25° C. and close to 0.2 (50/50 v/v) at 40° C., which corresponds to a viscosity 2 to 3 times higher than that of pure water or of pure ethanol.

Sub-nanometer-scale size measurement (DOSY NMR scattering experiments) reveals variations for the paracetamol molecule.

The particular composition of water-ethanol mixtures in the 50/50 (v/v) range leads to the smallest size for paracetamol, particularly at 40° C., the temperature closest to that of the human body. This can be interpreted by a low wetting of the molecule which would make it stealthier and give it a more hydrophobic character, helping its passage through membrane barriers, also hydrophobic.

The contraction of the paracetamol molecule, its stealth, combined with a high viscosity of the preparation and an effect of fluidification of biological membranes by ethanol, a known but poorly characterized phenomenon, contribute to the efficacy of the pharmaceutical formulations according to the invention in buccal/gingival administration.

2. Transport of Paracetamol Across the Blood-Brain Barrier
   Materials and Methods
   Materials
   A. Paracetamol Solutions
   U 95: 95 mg/ml paracetamol solution in a water/ethanol mixture (50/50 v/v) (C=628 mM), and
   PERFALGAN: 10 mg/mL commercial paracetamol solution for infants and children+excipients (C=66 mM).
   B. Cellular Model of the Blood-Brain Barrier
   It has previously been established in the literature that the hCMEC/D3 cell line may constitute a relevant in vitro model of the blood-brain barrier, which mimics the components of the latter [Weksler et al., FASEB J. 2005 November; 19(13):1872'4. Epub 2005 Sep. 1; Weksler et al., Fluids Barriers CNS. 2013 Mar. 26; 10(1):16. doi: 10.1186/2045'8118'10'1].

Figure 4:
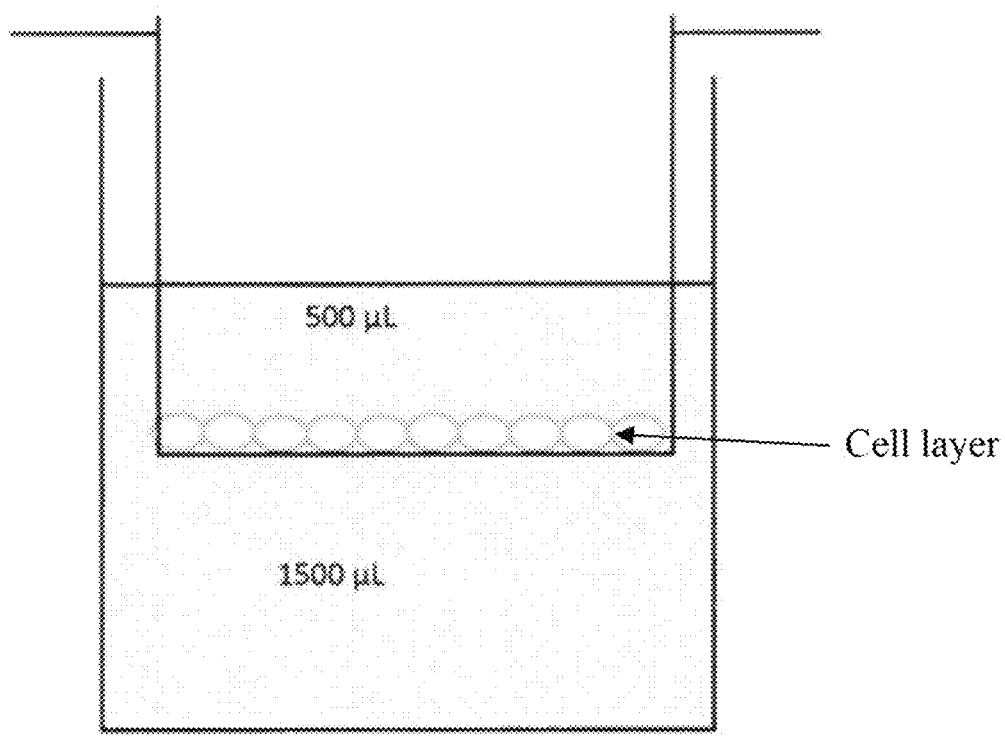

The cells were first cultured in cell culture vials (three passages of the culture after thawing frozen cells from the stock culture) and then seeded into the transwell system described in FIG. 4.

Once they reach confluence, which is obtained after 14 days of culture in the transwell system, the cells express the proteins characteristic of blood-brain barrier formation, namely ZO1, occludin, phalloidin and CD31.

The permeability of the barrier thus mimicked is then determined using Lucifer yellow. In this case, the Lucifer yellow does not manage to cross it.

C. Culture Medium

The composition of the culture medium is indicated in Table 3 below:

TABLE 3

Composition of the culture medium

| Solution in EBM2 | Volume (mL) |
|---|---|
| Fetal calf serum (5%)* | 25 |
| Antibiotics (penicillin and streptomycin) | 5 |
| Ascorbic acid (5 µg/mL) | 2.5 |
| Lipids (1/100) | 5 |
| HEPES (10 mM) | 5 |
| bFGF (1 ng/mL) | 2.5 |
| hydrocortisone (1.4 µM) | 0.25 |
| QS EBM2 | 500 |

*Some experiments, detailed below, were performed in the absence of serum, or with higher serum concentrations (20% and 50%).

D. HPLC

A specific HPLC method was developed to allow the quantification of paracetamol crossing the in vitro blood-brain barrier model described above, taking into account the culture medium and the sampling protocol.

The equipment used consists of a P4000 pump, a 6000LP UV detector with a 50 mm optical path, an AS 3000 autosampler with a 100 µL loop and an SN 4000 System Controller from Thermo Fisher (Courtaboeuf, France). The acquisition software used is ChromQuest 5.0.

The method developed is based on the following characteristics:
   Column: XTerra RP18 20*4.6 mm*3.5 µm,
   UV detector: 242 nm,
   Flow rate: 1 mL/min,
   Column temperature: 35° C.,
   Injected volume: 10 µL, and
   Mobile phase: ammonium formate buffer at 0.02 M and pH 4.

Methods

The following sampling protocol was established, which involves the different steps:
a) Deposition of 104 µL of U 95 in the upper compartment of the transwell system described in FIG. 4, b) Removal of 1000 μL from the lower compartment,
c) Protein precipitation by adding 200 μL of a 10% trichloroacetic acid solution,
d) Centrifugation at 3000 rpm for 10 min,
e) 1/10 dilution using the mobile phase,
f) Filtration using a 0.22 μm PTFE filter,
g) Injection of 10 μL into the HPLC, and
h) Quantification of paracetamol.

Results

Comparison of Blood-Brain Barrier Crossing by Paracetamol "U 95" Vs. Paracetamol "Perfalgan"

The flow of paracetamol through the in vitro model of the blood-brain barrier membrane was determined for both the paracetamol contained in the "U 95" solution and the paracetamol contained in the Perfalgan.

In order to have identical concentrations of paracetamol, in the first case, 10 μL of U 95 solution and 854 of culture medium were added to the luminal compartment of the transwell system, and in the second case, 954 of Perfalgan was used.

The crossing of each of the compounds was studied at 37° C. in the presence of saline in the culture medium (5%), and in the absence of saline.

The cells were cultured at 37° C. for 20-22 h before the measurements were taken.

Figure 5:
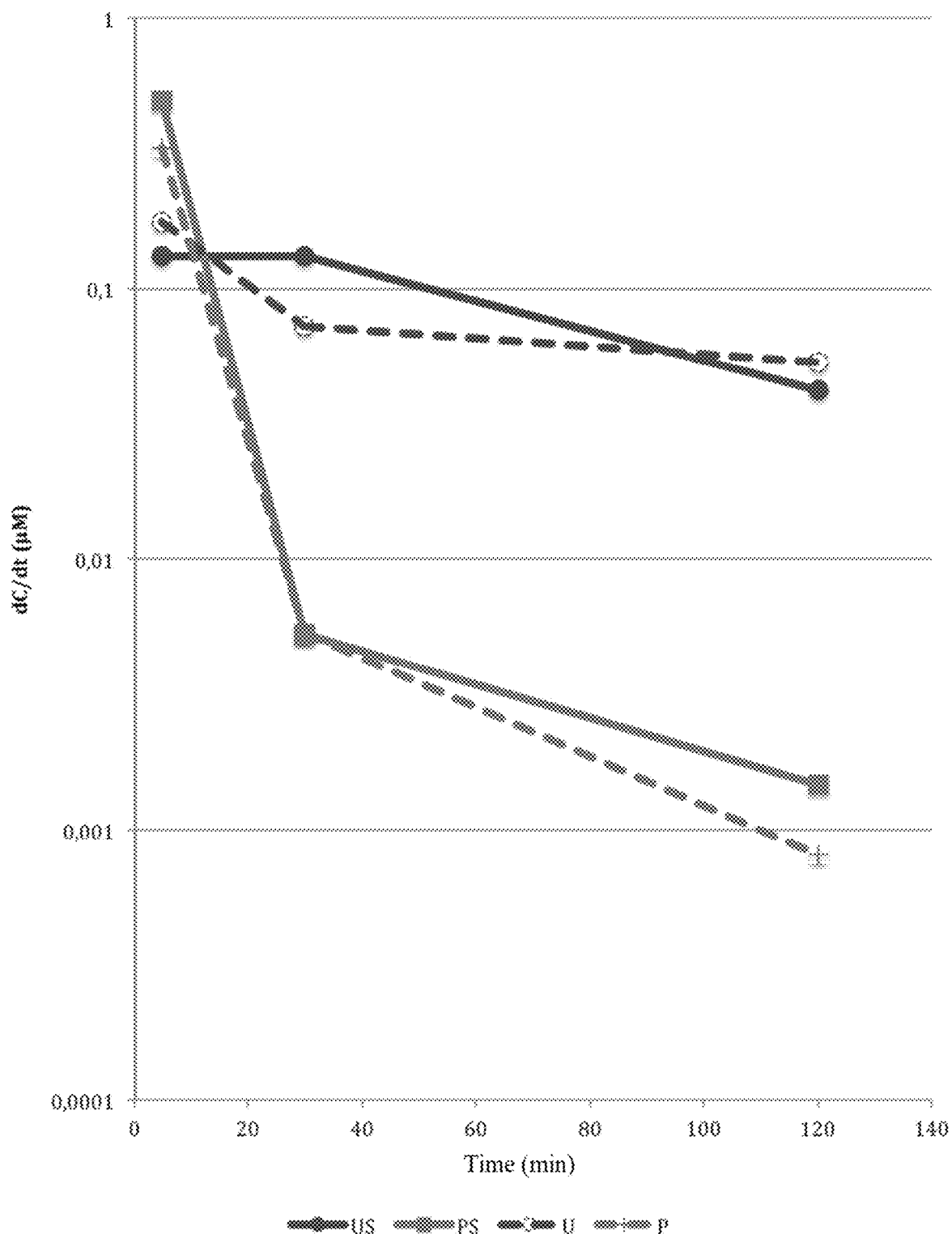

The flows thus determined have been reported in FIG. 5.

It can be seen that the flow of paracetamol "U 95" in the presence or absence of saline (curves US and U, respectively) is almost constant over time, and significantly higher than that of paracetamol "Perfalgan", which decreases very rapidly.

It is also noted in FIG. 5 that the transport of paracetamol "U 95" across the in vitro model of the blood-brain barrier membrane is higher in the presence of saline during the first 30 minutes.

Additional experiments were therefore carried out to determine the influence of saline on the transport of the transport of paracetamol "U 95".

Transport of Paracetamol "U 95" in the Presence of Saline

The change in the abluminal concentration of paracetamol "U95" over time was determined for saline contents in the cell medium of 0%, 5%, 20% and 50%.

Figure 6:
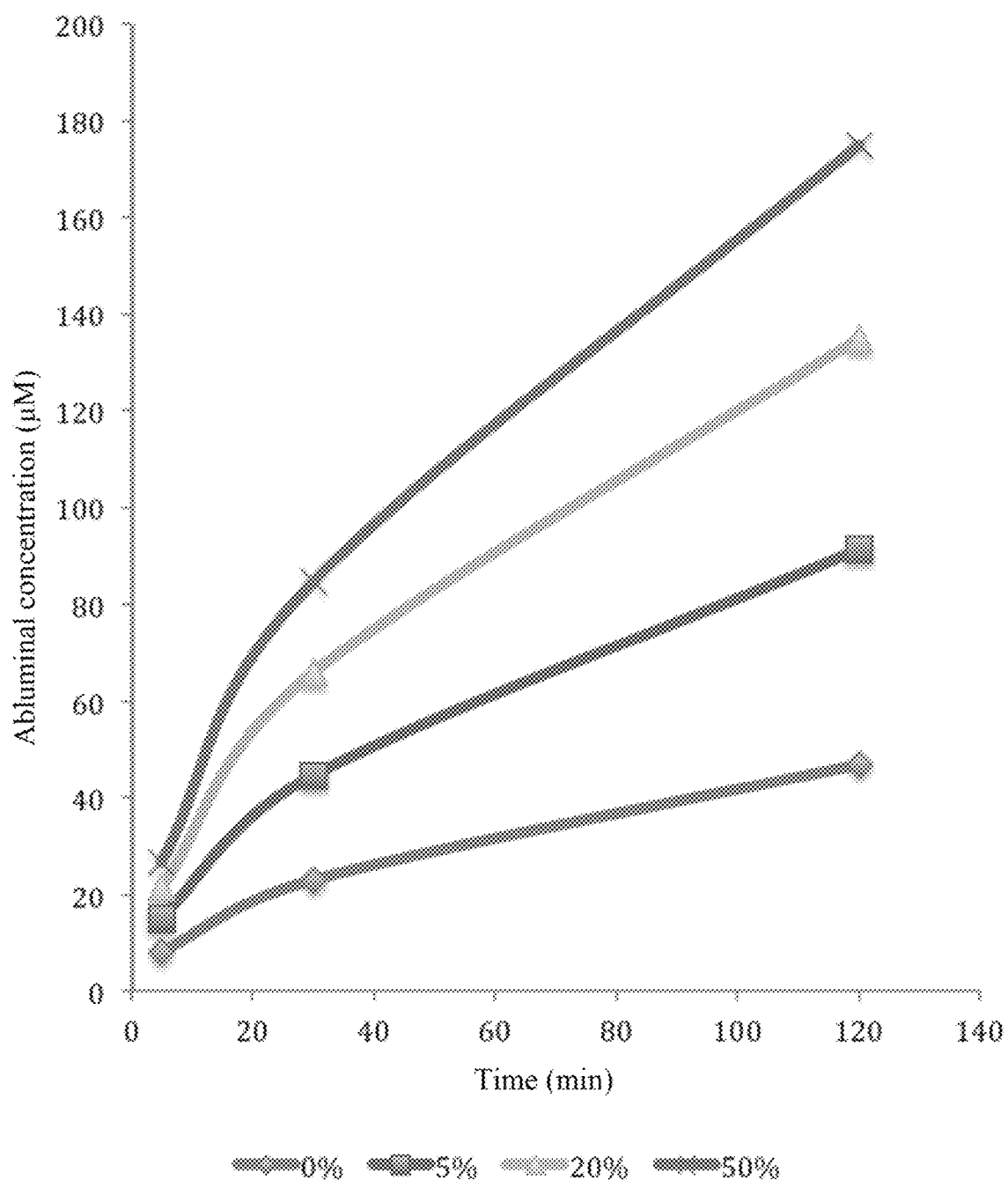
FIG. 6 shows the change in the abluminal concentration (i.e. in the lower compartment of the transwell) of paracetamol "U95" over time, for saline contents in the culture medium of 0%, 5%, 20% and 50%.

The results obtained have been reported in FIG. 6.

It should be noted that the values of abluminal concentrations of paracetamol shown in FIG. 6 correspond to the raw values obtained by HPLC quantification. Due to the dilution performed for HPLC, they should be multiplied by a factor of 12 to correspond to the actual values.

It can be seen that the transport of paracetamol "U 95" across the in vitro model of the blood-brain barrier membrane is enhanced by the presence of saline in the culture medium. It would even seem that there is a proportionality relationship between the amount of saline present and the amount of paracetamol that crosses the barrier.

On the other hand, such an influence of the presence or absence of saline is not observed for paracetamol "Perfalgan".

Indeed, the change in the abluminal concentration of paracetamol "Perfalgan" over time was determined for saline contents in the cell medium of 0%, 5%, 20% and 50%.

Figure 7:
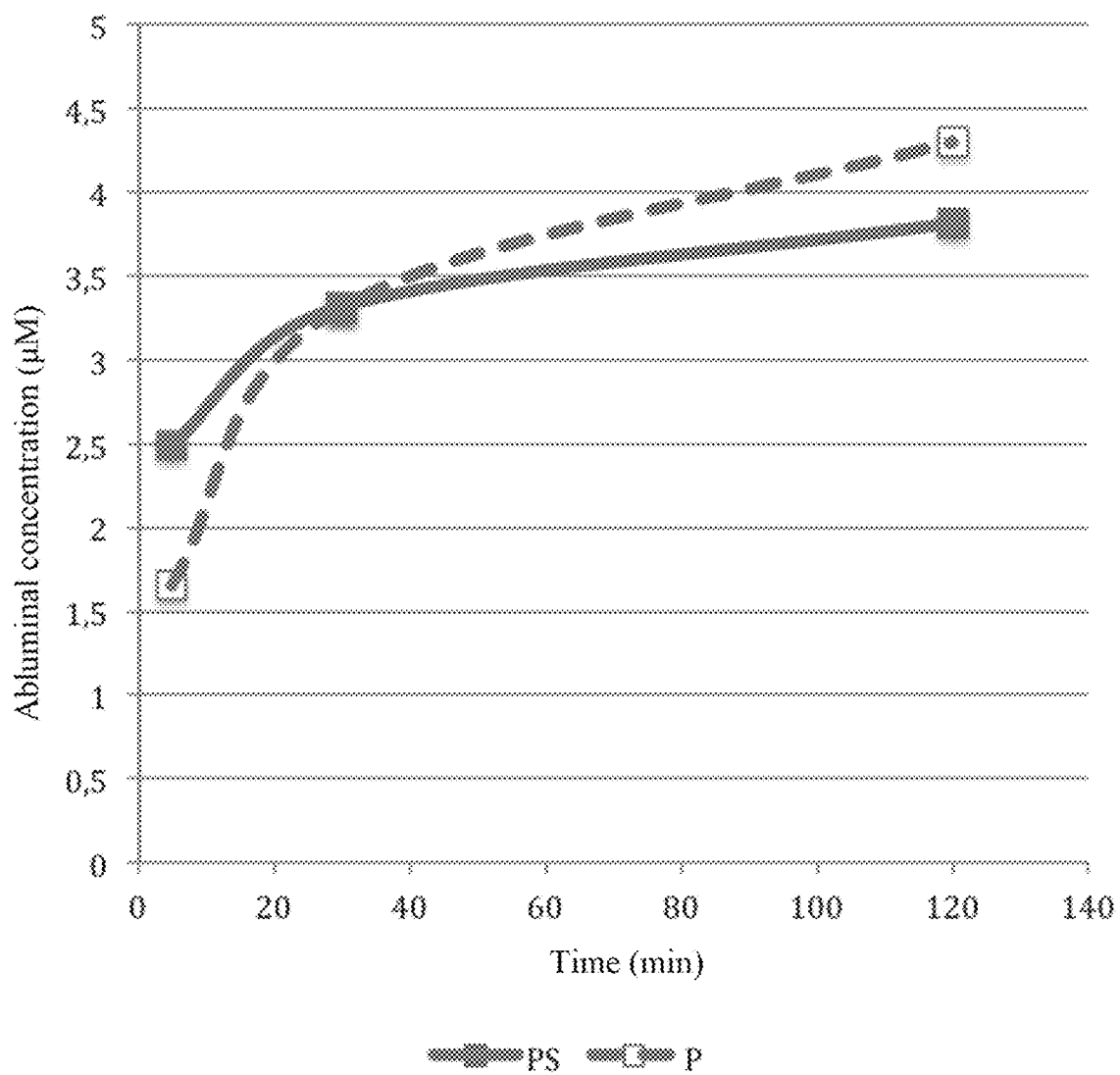
FIG. 7 shows the change in the abluminal concentration (i.e. in the lower compartment of the transwell) of paracetamol "Perfalgan" over time, depending on whether saline is present in the culture medium (5%, curve PS), or not (curve P).

The results obtained have been reported in FIG. 7.

It can be seen that the transport of paracetamol "Perfalgan" across the in vitro model of the blood-brain barrier membrane is less favorable in the presence of saline from 30 min.

CONCLUSION

The results described above show an active transport of the paracetamol contained in the pharmaceutical formulations according to the invention, in which at least one component of the saline solution is involved.

The invention claimed is:

1. A pharmaceutical formulation for the buccal/gingival administration of paracetamol consisting of a hydroalcoholic solution comprising dissolved paracetamol, wherein:
   the mass of paracetamol is between 120 mg and 170 mg,
   the volume of said hydroalcoholic solution is between 1.2 mL and 1.7 mL,
   the alcohol content of said hydroalcoholic solution is between 48.5° and 52.5°, and
   the concentration of paracetamol in said hydroalcoholic solution is between 90 mg/mL and 105 mg/mL, and
   the hydroalcoholic solution consists of a water/ethanol mixture having a viscosity greater than $1.5 \cdot 10^{-3}$ Pa·s,
   and wherein the hydrodynamic radius at 40° C. of the paracetamol is less than 2.1 Å.

2. The pharmaceutical formulation according to claim 1, wherein the volume of ethanol represents 50% of the total volume of said hydroalcoholic solution.

3. The pharmaceutical formulation according to claim 1, wherein the hydroalcoholic solution comprises a flavoring and/or a sweetener.

4. A method for the treatment of pain and/or fever comprising the administration to a person in need thereof of a pharmaceutical formulation according to claim 1.

5. A method for accelerating the crossing of the blood-brain barrier by paracetamol comprising the buccal/gingival administration of a pharmaceutical formulation consisting of a hydroalcoholic solution comprising dissolved paracetamol, wherein:
   the mass of paracetamol is between 120 mg and 170 mg,
   the volume of said hydroalcoholic solution is between 1.2 mL and 1.7 mL,
   the alcohol content of said hydroalcoholic solution is between 48.5° and 52.5°, and
   the concentration of paracetamol in said hydroalcoholic solution is between 90 mg/mL and 105 mg/mL, and
   the hydroalcoholic solution consists of a water/ethanol mixture having a viscosity greater than $1.5 \cdot 10^{-3}$ Pa·s,
   and wherein the hydrodynamic radius at 40° C. of the paracetamol is less than 2.1 Å.

6. The method according to claim 5, wherein the volume of ethanol represents 50% of the total volume of said hydroalcoholic solution.

* * * * *